United States Patent [19]
Polyak

[11] Patent Number: 4,865,030
[45] Date of Patent: Sep. 12, 1989

[54] APPARATUS FOR REMOVAL OF OBJECTS FROM BODY PASSAGES

[75] Inventor: Mark Polyak, Minnetonka, Minn.

[73] Assignee: American Medical Systems, Inc., Minnetonka, Minn.

[21] Appl. No.: 6,730

[22] Filed: Jan. 21, 1987

[51] Int. Cl.$^4$ ............................................. A61B 17/52
[52] U.S. Cl. .................................... 128/321; 128/328; 128/356; 294/2; 294/65.5; 294/100
[58] Field of Search ........... 128/321, 356, 328, 303 R; 294/65.5, 2, 100

[56] References Cited

U.S. PATENT DOCUMENTS

| | | | |
|---|---|---|---|
| 1,651,258 | 11/1927 | Deffenbaugh | 294/100 |
| 2,683,618 | 7/1954 | Long | 294/65.5 |
| 3,332,425 | 7/1967 | Luborsky et al. | 128/356 |
| 3,372,695 | 3/1968 | Beliveau et al. | 128/1 |
| 3,503,400 | 3/1970 | Osthagen et al. | 128/349 |
| 3,811,450 | 5/1974 | Lord | 128/349 R |
| 3,812,841 | 5/1974 | Isaacson | 128/1 R |
| 4,509,517 | 4/1985 | Zibelin | 128/319 |
| 4,572,162 | 2/1986 | Livesay et al. | 128/1 R |
| 4,727,866 | 3/1988 | Livesay et al. | 128/130 |

FOREIGN PATENT DOCUMENTS

| | | | |
|---|---|---|---|
| 153021 | 8/1985 | European Pat. Off. | |
| 709732 | 8/1941 | Fed. Rep. of Germany | |
| 1197974 | 12/1985 | U.S.S.R. | 294/2 |
| 1271814 | 11/1986 | U.S.S.R. | 294/2 |

OTHER PUBLICATIONS

Article entitled "Use of Completely Implantable Urethral Catheter in Male Patients With Spinal Cord Injury", by R. S. Munro, F. B. Scott, *Urology*, 11/76, vol. VIII, No. 5.
Advertisement in *Urology Times*, 3/87, pp. 14–15.

*Primary Examiner*—Michael H. Thaler
*Attorney, Agent, or Firm*—Peter C. Richardson; Lawrence C. Akers; Mark Dryer

[57] ABSTRACT

An apparatus for insertion into the urethra for attachment to and removal of an in-dwelling urinary continence device comprises generally a tubular body having a longitudinal bore with a slidable shaft therein. Slidable jaws are connected to a first end of the shaft and are normally retained in a closed position within the bore. The shaft may be longitudinally displaced within the bore to cause the jaws to protrude therefrom and assume an opened position. A magnet, slidable within the jaws, protrudes from the jaws when they are in their opened position to attract a ferrous ball for retraction into the jaws. The apparatus employs a method for removing an intraurethral device wherein anchoring members holding the device in place may be collapsed and the device removed with a single insertion of the tool. The device may also be used for retrieving objects from body passages other than the urethra, for example, arteries.

20 Claims, 3 Drawing Sheets

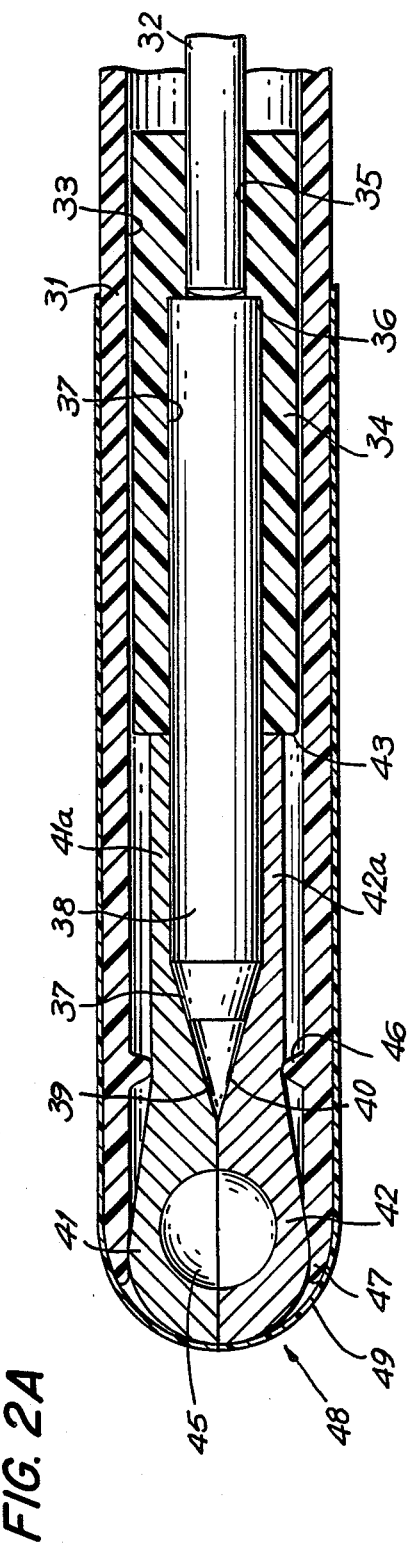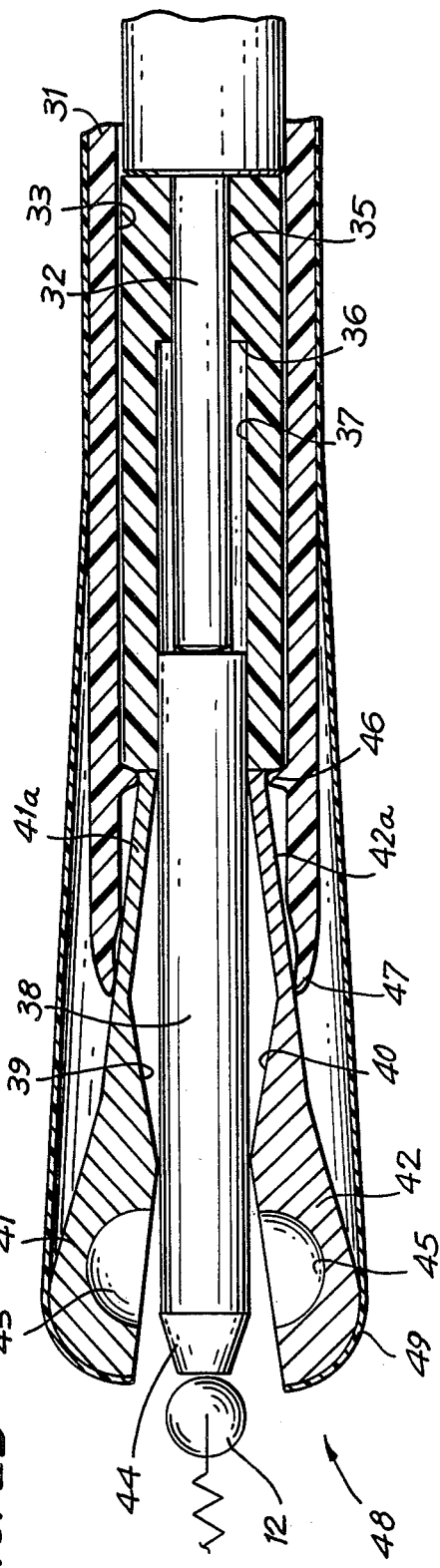
FIG. 2A
FIG. 2B

APPARATUS FOR REMOVAL OF OBJECTS FROM BODY PASSAGES

BACKGROUND OF THE INVENTION

The present invention relates to a method and apparatus for removing in-dwelling urethral devices generally used to achieve urinary continence. More particularly, an apparatus is designed to engage such a device in a manner which enables the device to be dislodged and withdrawn from the urethra. The apparatus is especially characterized by its application of a combination of magnetic and mechanical features and will find application in removing objects from body passages other than the urethra.

FIELD OF THE INVENTION

Urinary incontinence is a serious and long-recognized problem in the medical field, and much effort has been directed to providing devices for handling the problem. The number of patents granted in this field is evidence of such efforts.

Urinary incontinence is the inability to voluntarily control the elimination function of the bladder. This problem can result from numerous causes, including old age, disease, trauma, or some form of neurological dysfunction, and the problem is generally incurable. The patient suffering from urinary incontinence may experience embarrassment, discomfort, and loss of self-esteem. In addition, normal human activity may be severely limited.

Attempts to alleviate this problem have generally involved external, external/internal, or completely in-dwelling devices. Examples of external devices are adult diapers and urine alarms. External/internal devices such as urinary catheters have also been studied. These several types of devices have numerous well-known disadvantages, including susceptibility to infection and discomfort and embarrassment to the wearer.

Because of the many disadvantages of external and external/internal devices, completely in-dwelling devices have become more favored for achieving urinary continence. Although many of the in-dwelling devices have their own drawbacks, susceptibility to infection, odor, and embarrassment are generally lessened. However, a serious drawback which remains is that of insertion and removal of the device.

Although in-dwelling devices are generally designed for long-term use, periodic removal may be required to prevent damage to the urethra, the bladder, or the prostate area. Cystoscopes have been used to grasp the urinary continence device in the urethra so that it can be removed, but that procedure requires special facilities, is time-consuming and is expensive.

A device is desired which can be inserted into the urethra without significant difficulty or trauma. Such a device will be pliable and of relatively small diameter to facilitate its movement through areas of restricted diameter in the urethra. The device will preferably attach itself to a urinary continence device quickly and easily and retain the device in its grip for disengagement and removal.

The apparatus of the present invention is especially intended for use with in-dwelling urethral devices which employ inflatable balloons, collars, sleeves or other anchoring means for holding the devices within a urethra. After such a device is inserted into the urethra, the anchor means are forced against the wall of the urethra and left in that condition until removal of the device is desired. In some instances, an inflatable anchor is simply punctured, and a special tool is then used to lock onto the device for pulling it from the urethra. In the case of the present invention, features are incorporated in both the anchor member and the removal tool which enable the anchor member to be readily engaged, collapsed, dislodged and withdrawn. A single removal tool employs a method designed to carry out all of these operations during the course of a single insertion of the tool.

SUMMARY OF THE INVENTION

A removal tool according to the present invention generally comprises a tubular body having a longitudinal bore for receiving a sliding shaft. The rearward end of the shaft protrudes from one end of the bore, and a knob is attached to that end of the shaft. The other, forward end of the shaft terminates inside the bore of the body within a grasping mechanism. The grasping mechanism is integral with a sliding sleeve which generally houses a cylindrical magnet. The shaft extends into the sleeve and is joined to one end of the magnet. The grasping mechanism comprises jaws which, at their rearward or pivot end, define a generally conical bore and, at their forward end, define a cavity for gripping or trapping objects.

As mentioned above, the removal tool of the invention is especially useful with in-dwelling urethral devices which employ inflatable anchor members. The anchor members are provided with pull plugs, caps or similar closure members which seal off openings in the anchor members. The closure members in turn are attached through short tethers or the like to small magnetically permeable members, preferably spherical. The permeable members are conveniently made of an iron-containing material, preferably unaffected by fluids which they may contact while in use. The closure members, in addition to being attached to permeable ball members, are also attached to their urethral devices, so that pulls on the ball members translate into pulls on the urethral devices.

In using the removal tool, the forward end of the tubular body is inserted into the urethra to a position near the ball member of the urethral device. Using the knob of the removal tool, the shaft of the tool is made to slide further into the bore of the tool, thereby forcing the magnet into the conical bore of the jaws. The jaws are made to open, and the magnet is made to protrude sufficiently from the jaws to attract the ball attached to the closure member of the inflated anchor of the urethral device. The magnet and the ball are then withdrawn back into the jaws by pulling on the knob, whereupon the ball is captured in the spherical cavity as the jaws are retracted into the tubing body. After the ball has been captured and the jaws retracted, the removal tool is pulled slightly to release the closure means and deflate the anchors and is then withdrawn from the urethra together with the urethral device.

Other applications of the present invention will facilitate removal of objects from body passages other than the urethra. For example, objects may be retrieved from arteries or the esophagus. Other uses will become obvious upon review of the following detailed description of one embodiment of the invention.

BRIEF DESCRIPTION OF THE DRAWINGS

FIGS. 2A and 2B are enlarged cross-section views of the grasping mechanism of the removal tool, FIG. 2A showing the mechanism in its closed position and FIG. 2B showing the mechanism in its open position.

DETAILED DESCRIPTION OF A PREFERRED EMBODIMENT

Figure 1:
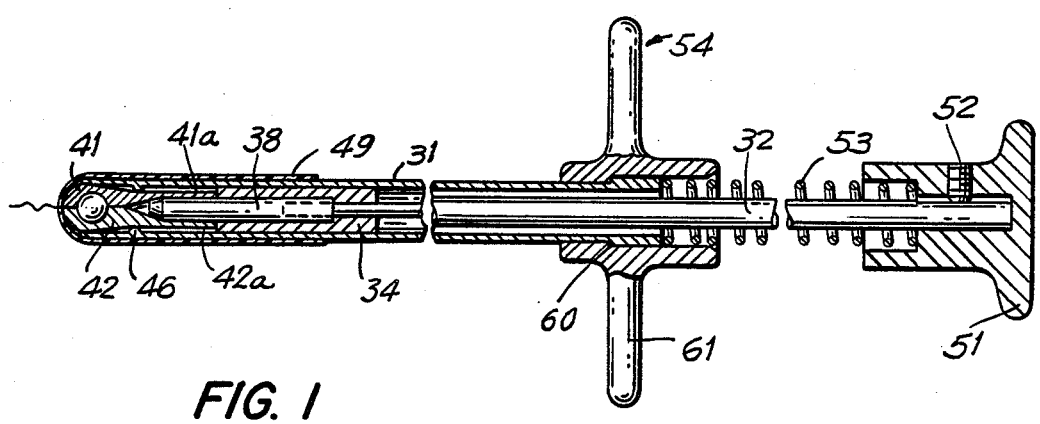
FIG. 1 is a cross section of a removal tool according to the present invention.

Referring to FIGS. 1, 2A and 2B, one embodiment of the present removal tool generally comprises a tubular body 31 with a longitudinal bore 33 therethrough. The bore 33 has a substantially uniform diameter. The body 31 may be formed of silicone or other relatively soft flexible material. The overall diameter of body 31 is relatively small, so that it may be used in the urethra or other narrow body passage without undue discomfort or trauma.

A magnet enclosure 34 is a cylindrical sleeve-like member inserted in the bore 33 and is slidable therein along the longitudinal axis of the bore 33. Because the bore 33 has a substantially uniform diameter, the enclosure 34 may generally slide the length of the bore 33, although, as will be more fully described below, its forward movement is limited by a tubing stop 46.

The enclosure 34 has a first or plunger bore 35 and a second or magnet bore 37, each concentric with the bore 33 and aligned along the longitudinal axis of the enclosure 34. The bores 35 and 37 have a shoulder 36 therebetween. The shoulder 36 is circumferential about the bore 37 and lies in a plane perpendicular to the longitudinal axis of the bores 35 and 37.

A magnet 38 is cylindrical in shape and is slidably positioned within the bore 37. In its fully withdrawn position, the aft end of the magnet 38 abuts the shoulder 36. The bore 37 and the magnet 38 both have a greater diameter than the bore 35.

Extending through the bore 33 of the body 31 and through the bore 35 of the enclosure 34 is a plunger or shaft 32. The shaft 32 is generally rod-like in shape and may protrude past the shoulder 36 into the bore 37. A first, distal, or forward end of the shaft 32 which extends through the bore 35 to the shoulder 36 is joined to a first, rearward, or proximal end of the magnet 38 positioned within the bore 37. Thus, longitudinal movement of the plunger 32 within the bores 33 and 35 causes corresponding longitudinal movement of the magnet 38 within the bore 37 and may cause the magnet 38 to extend out of the bore 37. As mentioned above, longitudinal movement of the magnet 38 into the bore 37 is limited by the shoulder 36.

A second, distal, or forward end of the magnet 38 has its circular edge bevelled, indicated at 44, so as to engage the interior faces 39 and 40 of jaw halves 41 and 42 in a manner to be more fully described.

The jaws 48 include jaw halves 41 and 42 which join to form balloon-shaped jaws having a generally smooth outer surface for sliding in and out of the tubing 31. Semi-cylindrical arms 41a and 42a of the jaw halves 41 and 42, respectively, abut and join to an end face of the enclosure 34 adjacent the bore 37. The arms 41a and 42a join to form a cylindrical shape having a bore 37a of diameter substantially equivalent to that of the bore 37 and aligned along the same longitudinal axis. The outside diameter of the cylinder shape formed by the arms 41a and 42a is smaller than the outside diameter of the enclosure 34, resulting in a circumferential shoulder or jaw step 43 at the junction with the enclosure 34.

The bore 37a terminates interior to the jaw halves 41 and 42 in a cone with faces 39 and 40 defining the surface of the cone. The faces 39 and 40 are each semi-conical and extend from the outer diameter of the bore 37a at their base to the longitudinal axis of the bore 37a at their apex.

The magnet 38, when the plunger 32 is displaced longitudinally inward, is able to extend into the bore 37a of the jaws 48 such that the bevelled edge 44 will engage the faces 39 and 40. As can be seen in FIG. 2B, continued longitudinal displacement of the shaft 32 will cause the jaws 48 to extend out of the tubing 31 and will cause the edge 44 of the magnet 38 to force the faces 39 and 40 forward and apart, separating the jaw halves 41 and 42 and opening the jaws 48. The magnet 38 may then protrude through the open jaws 48 and attract an object such as a ferrous ball 12.

Contained within the jaws 48 is a cavity 45. The cavity 45 may be formed by two hemispherical cavities, one formed in each of the jaw halves 41 and 42. When the jaws 48 are opened by longitudinal movement of the magnet 38, the cavity 45 is opened and capable of receiving an object such as a ball 12. When the jaws 48 are closed, the cavity 45 is a closed sphere which may trap or hold a ball or other object.

The enclosure 34 and the jaws 48 together make up a generally cylindrical grasping mechanism or receptacle having bores 37 and 37a internal thereto for housing the magnet 38 which is slidable within the bores. The grasping mechanism or receptacle is itself slidable within the bore 33, limited by the tubing stop 46. The shaft bore 35 in the enclosure 34 receives the shaft 32 for connection to the magnet 38. Moving together, the shaft 32 and the magnet 38 serve to actuate the jaws 48 from their normally-closed first position to an open second position for receiving objects in the cavity 45.

In their normal or closed position, the jaws 48 are withdrawn into the tubing 31 with an end of the tubing 31 having a circumferential lip 47 generally encircling the jaws 48. Adjacent the lip 47 and internal to the bore 33 is an inwardly projecting tubing stop 46 which is situated about the circumference of the bore 33. The tubing stop 46 engages the jaw step 43 when the enclosure 34 is moved toward the lip 47, and thereby limits the longitudinal movement of both the enclosure 34 and the jaws 48. In this forward position, the jaws 48 protrude past the lip 47 and out of the bore 33 and are in position to open in response to further forward movement of the shaft 32 in the bore 33.

Overlaying the tubing body 31 and extending substantially its length is a sleeve or skin 49. The sleeve 49 functions as a skin and may be constructed of silicone or similar material capable of stretching. In instances where the jaws 48 are allowed to protrude slightly from the bore 33, the skin 49 preferably extends over the lip 47 for joinder to the jaw halves 41 and 42. With such a construction, the skin 49 will stretch as the jaws 48 are extended out of the bore 33 and will regain its normal form as the jaws 48 are once again withdrawn into the bore 33. The sleeve 49 may be used to cover the lip 47 and provide a smooth surface without edges for insertion into a urethra.

The end of body or tubing 31 opposite the jaws 48 terminates in a disk or handle 54. The handle 54 may be joined to the tubing 31 in a variety of well known ways, including the use of shoulders 60 external to the tubing 31 and internal to the handle 54 for mutual engagement. The tubing 31 and the handle 54 may also be joined using various bonding means.

The shaft 32 extends beyond the bore 33 and through the handle 54 and terminates in a knob 51 which is longitudinally spaced from the handle 54. The knob 51 is retained on the shaft 32 using a set screw 52 or other suitable means. Intermediate the handle 54 and the knob 51 is a spring 53 tending to maintain a separation between the handle 54 and the knob 51. The spring 53 thus biases the magnet 38 in a withdrawn position within the enclosure 34 and biases the jaws 48 toward a closed position within the tubing 31.

The handle 54 may include grips 61 for use in conjunction with the knob 51 to compress the spring 53. Moving the knob 51 toward the handle 54 causes the shaft 32 to slide within the bore 33. The magnet 38 is thereby made to actuate the jaws 48 as described above.

Figure 3:
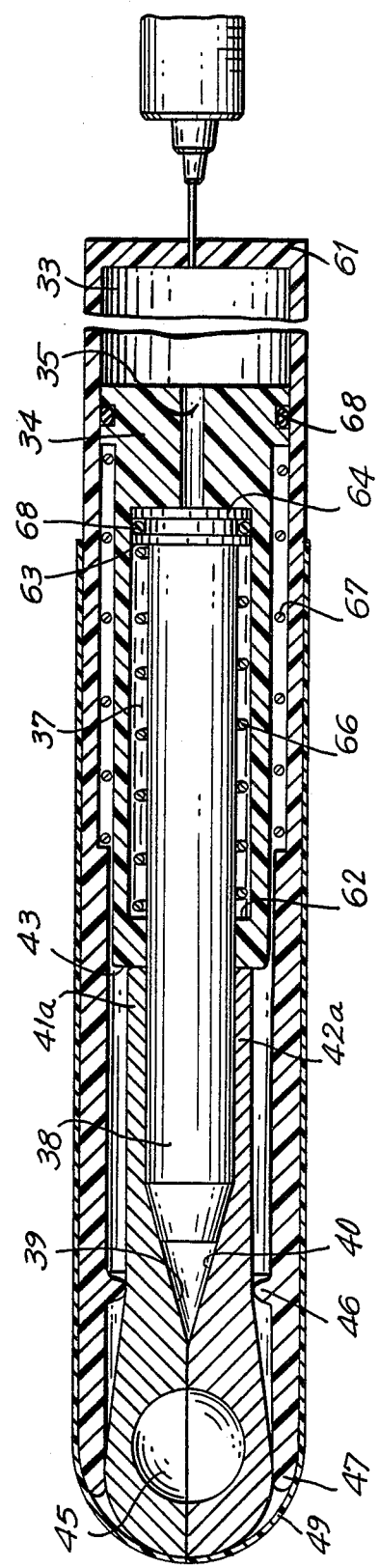
FIG. 3 is a cross-section view of an alternate embodiment of a removal tool according to the present invention.

FIG. 3 shows an alternate embodiment of the present invention wherein the shaft 32 of FIGS. 1 and 2 has been eliminated. The mechanism for actuating the jaws 48 and the magnet 38 may be pneumatic or hydraulic in nature. The rearward end 61 of the body 31 is adapted to receive a syringe or similar means for injecting a liquid or gaseous substance into the bore 33. The injected substance, preferably a relatively incompressible material, begins to fill the bores 33 and 35.

When sufficient pressure has developed in the bores 33 and 35, the magnet 38 is forced forward into abutting relationship with the surfaces 39 and 40 on the interior of the jaws 48 and the magnet enclosure 34 is forced forward until shoulder 43 abuts the stop 46. The injection of additional fluid or gas into the bore 33 results in an increasing pressure within bores 33, 35 and 37. Again, when sufficient pressure has developed, the magnet 38 forces the jaws 48 open and the magnet 38 may protrude through the open jaws 48.

The magnet 38 is prevented from completely exiting the jaws 48 by means of cooperating shoulders 62 and 63 on the magnet enclosure 34 and the magnet 38, respectively, by similar means.

As in the preferred embodiment shown in FIG. 1, when the magnet 38 protrudes through the open jaws 48, it may attract a ferrous ball which is connected to a urethral device. When the object has been attracted by the magnet 38, the pressure within the bores 33, 35 and 37 may be released by withdrawal of the syringe from the body 31 or by any other suitable method.

Springs 66 and 67 connected between the magnet 38 and the enclosure 34 and between the enclosure 34 and the body 31 bias the magnet 38 and the enclosure 34 toward a position within the bore 33. As in the case of the preferred embodiment shown in FIGS. 1, 2A and 2B, the jaws 48 are biased toward a closed position by the nature of their connection to the enclosure 34 and by the inwardly directed radial force exerted by the lip 47 and the body 31 as the jaws 48 are withdrawn into the bore 33.

The enclosure 34 and the magnet 38 may be provided with circumferential seals 68 to prevent the escape of fluid or gas pressure as the magnet 38 and the jaws 48 are actuated. It will be obvious to those skilled in the art that other suitable means may be utilized for the purpose.

The embodiment illustrated in FIG. 3 provides remote control of the capturing mechanism and will have an advantage in that it may generally be made of a smaller overall diameter because an internal shaft is not needed. However, certain disadvantages, such as reliability and controllability, may be realized.

OPERATION OF THE DEVICE

A removal tool according to the present invention may be utilized to remove a urinary continence device which includes inflatable anchors for retaining the device in position within a urethra. Generally, such a device may include a pull plug on its lower end which, when removed from its plugging position, allows anchoring collars to deflate so that the device may be withdrawn from the urethra. In accordance with the device, the pull plug may have attached to it a ball or other object which may be easily grasped and pulled. The tool illustrated in FIG. 1 is designed for use with such a continence device.

Figure 4:
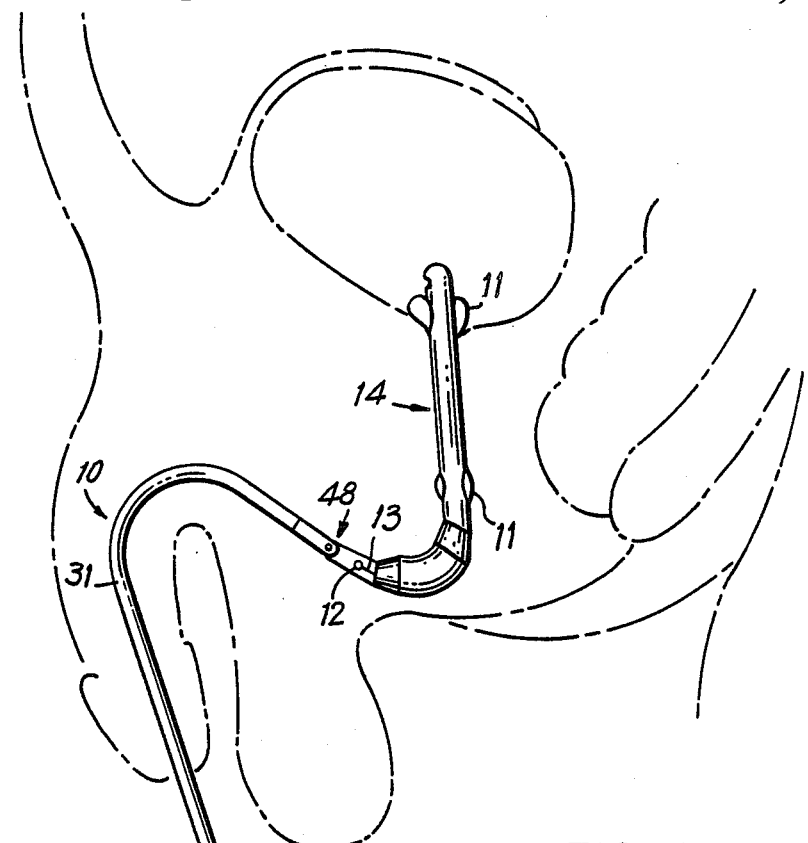
FIG. 4 is a section view of a male urethra with a urinary continence device in place and a removal tool inserted for removing the continence device.
Figure 4:
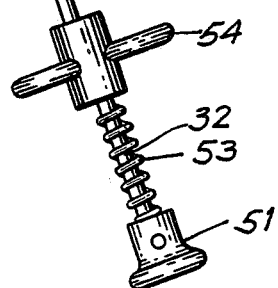

FIG. 4 illustrates a urinary continence device 14 positioned within a male urethra and having a small ball 12 of ferrous material or material containing ferrous inserts attached to its pull plug (not shown) by means of a suture 13. A removal tool 10 is shown in position within the urethra and the jaws 48 are shown in position near the ferrous ball 12.

When it is desirable to remove the continence device 14 from the urethra, the removal tool 10 is inserted into the urethra and is guided along the urethra to the ball 12 attached to the pull plug. The tubular body 31 is of a soft pliable material so that it may be inserted through the urethra without significant difficulty or trauma. When the proximal or forward end of the tool 10 nears the ferrous ball 12, the knob 51 is pushed toward the handle 54, compressing the spring 53 and urging the shaft 32 into the bore 33. As the magnet 38 is urged toward the faces 39 and 40 of the jaws 48, the enclosure 34 and the jaws 48 are caused to move forward protruding from the bore 33 until the jaw step 43 encounters the tubing stop 46. The tubing stop 46 limits the forward, outward projection of the jaws 48 and continued longitudinal movement of the shaft 32 and the magnet 38 causes the magnet 38 to part the jaw halves 41 and 42, opening the jaws 48. Further movement of the magnet 38 causes it to protrude from the open jaws and to attach itself to the ferrous ball 12.

When the ball 12 has been captured by the magnet 38, the knob 51 is withdrawn causing the magnet 38 to be once again withdrawn within the jaws 48. When the magnet 38 has been sufficiently withdrawn, the jaw halves 41 and 42 rejoin and the ball 12 is captured within the cavity 45. Continued withdrawal of the magnet 38 by pulling on the knob 51 results in the magnet 38 engaging the shoulder 36 and forcing a withdrawal of the jaws 48 into the tubing 31.

By applying a slight pulling force to the tool 10, the pull plug, being attached to the ball 12 by suture 13, is disengaged from the continence device 14, causing the inflatable cuffs or collars 11 to deflate. Once the anchoring mechanism for the continence device 14 has been released, a steady pull on the tool 10 will force a withdrawal of the device 14 from the urethra.

It will now be recognized that a new removal tool has been provided that can be conveniently utilized to remove a urinary continence device from a urethra without significant difficulty or trauma. Application of the invention will include tools for removing many types of objects from narrow body passages. Although the above description describes details of a preferred embodiment of the present invention, it will be understood by those skilled in the art that numerous other embodiments and applications of the invention may exist or be developed. For example, the body 31 may be eliminated and the enclosure 34 may be lengthened sufficiently to extend out of the urethra. The sleeve-like enclosure 34 will then function as both the body 31 and the enclosure 34. Although in many such applications, all of the advantages of the illustrated embodiment may not be achieved, certain desirable attributes may be attainable. The scope of the present invention should accordingly be limited only by the scope of the appended claims.

What is claimed is:

1. A removal tool for use in body passageways, comprising:
   a tubular sleeve adapted to be inserted into a passageway, said sleeve having a bore extending from its rearward end to its forward end;
   a shaft longitudinally slidable within said bore between a rearward position and a longitudinally spaced forward position;
   a magnet attached to a forward end of said shaft and slidable with said shaft in said bore; and
   normally closed jaws connected around the forward end of said sleeve and shaped internally to define a cavity for gripping or trapping an object, said jaws opening forward of said sleeve to enable said magnet to project forward of said cavity upon forward movement of said shaft through said bore.

2. The tool of claim 1, further comprising
   a relatively soft, flexible tubular body having a longitudinal bore for housing said tubular sleeve and said jaws.

3. The tool of claim 2, wherein said jaws are slidable between a first retracted position substantially within the forward end of said tubular body and a second extended position substantially forward of said forward end of said tubular body.

4. The tool of claim 1, further comprising
   a handle connected to the rearward end of said shaft external of the rearward end of said sleeve.

5. The tool of claim 4, further comprising
   a spring connected to said handle to resist forward movement of said shaft through said bore.

6. The tool of claim 1, wherein
   said sleeve includes a shoulder at its rearward end and projecting inwardly of said bore to define the rearwardmost position of said shaft relative to said sleeve.

7. The tool of claim 1, wherein
   said jaws comprise a plurality of jaw segments, said segments responsive to forward movement of said shaft to separate outwardly.

8. A grasping tool for use in a passageway, comprising:
   an elongated tubular body defining a central axial bore extending from a forward end to a rearward end of said body, said body adapted to be inserted into a passageway;
   an elongated shaft movably fitted within said bore to move between a rearward retracted position and a forward extended position;
   forward opening jaws positioned within the forward end of said bore, said jaws configured to open upon the application of forces directed radially outward against said jaws; and
   a magnet at the forward end of said shaft and configured to apply a radially outward force on said jaws upon movement of said shaft toward its forward position,
   with said jaws being slidable between a first retracted position within said bore and substantially within the forward end of said tubular body and a second extended position substantially external of said bore and substantially forward of said forward end of said tubular body.

9. The tool of claim 8, wherein
   said tubular body is tapered in thickness at its forward end to form a circumferential lip.

10. A grasping tool for use in a passageway, comprising:
    an elongated tubular body defining a central axial bore extending from a forward end to a rearward end of said body, said body adapted to be inserted into a passageway;
    an elongated shaft movably fitted within said bore to move between a rearward retracted position and a forward extended position;
    forward opening jaws positioned within the forward end of said bore, said jaws configured to open upon the application of forces directed radially outward against said jaws; and
    a magnet at the forward end of said shaft and configured to apply a radially outward force on said jaws upon movement of said shaft toward its forward position,
    said jaws being shaped internally to define a forward cavity and a rearward passageway, the interior of said passageway configured to receive said magnet such that said magnet applies an axial force to move the jaws forward and a radial opening force to said jaws upon forward movement of said shaft to thereby open said jaws and said cavity and enable said magnet to protrude through said cavity.

11. The tool of claim 10 in combination with an indwelling urethral device including an anchoring member to anchor said device within said urethra and a removable closure member for collapsing said anchor member, said closure member including a magnetically inductive material adapted to be retained within said cavity upon closing of said jaws.

12. A tool for removing an object from a passageway in a human or animal body, comprising:
    a tubular body adapted to be inserted into a passageway, said body having a forward end, a rearward end and a longitudinal bore therethrough;
    a normally-closed receptacle at said forward end of said body remotely operable from said rearward end of said body to open to receive an object from within said passageway, said object being received within a cavity in said receptacle; and
    a magnet normally positioned within said receptacle and remotely operable from said rearward end of said body to be extended to a position forward and external of said cavity when said receptacle is open and to be retracted into said receptacle.

13. The tool of claim 12, wherein
    said receptacle is slidable from a first, closed position within said bore to a second, open position forward and external of said bore.

14. The tool of claim 13, further comprising an injector for injecting a fluid into said bore for moving said receptacle to its said second, open position; and a spring for biasing said receptacle toward its said first, closed position.

15. The tool of claim 14, wherein said fluid is relatively incompressible.

16. The tool of claim 12, further comprising a shaft longitudinally movable within said bore and extending at its rearward end out from the rearward end of said bore, said shaft connected at its forward end to said magnet.

17. The tool of claim 16, wherein said magnet is configured to move said receptacle forward and open said receptacle upon forward movement of said shaft within said bore.

18. The tool of claim 16, wherein said magnet is configured to open said receptacle upon forward movement of said shaft within said bore.

19. A tool for use in removing an intraurethral device from a urethra which comprises:

a soft, flexible tubular body having forward and rearward ends corresponding to the front and rear of the tool and an axial bore extending between said ends, said body adapted at its forward end to be inserted into a urethra;

a tubular sleeve longitudinally movable between longitudinally spaced forward and rearward positions within said bore;

a set of normally closed, forward facing jaws fitted within said forward end of said bore and attached at their rearward ends to the forward end of said sleeve, said jaws configured internally to define a passageway substantially co-axial with said sleeve and extending forward into said jaws; said jaws further configured internally forward of said passageway to define a cavity;

a shaft fitted within said sleeve in longitudinally slidable relation with said sleeve, said shaft having a rearward end which extends beyond the rearward ends of said body and said sleeve; and a magnet attached at its rearward end to the forward end of said shaft and extending forward into said passageway to terminate in a configuration adapted to move forward and open said jaws and to pass forward of said cavity upon forward movement of said shaft relative to said sleeve when said sleeve is in its said forward position.

20. The tool of claim 19 in combination with an indwelling-type urethral device, said device comprising:

an anchor member to anchor said device in a urethra; and a removal member on said anchor member operable to collapse said anchor member, said removal member including a magnetically inductive material capable of being held by said magnet and also fitting within said cavity.

* * * * *